(12) United States Patent
Farhat et al.

(10) Patent No.: US 10,413,309 B2
(45) Date of Patent: Sep. 17, 2019

(54) SYSTEMS AND METHODS FOR CATHETER ADVANCEMENT

(71) Applicant: Covidien LP, Mansfield, MA (US)

(72) Inventors: Lawrence Farhat, Carlsbad, CA (US); Andy Huynh, Westminster, CA (US)

(73) Assignee: Covidien LP, Mansfield, MA (US)

( * ) Notice: Subject to any disclaimer, the term of this patent is extended or adjusted under 35 U.S.C. 154(b) by 126 days.

(21) Appl. No.: 15/654,888

(22) Filed: Jul. 20, 2017

(65) Prior Publication Data

US 2017/0311963 A1 Nov. 2, 2017

Related U.S. Application Data

(62) Division of application No. 14/254,063, filed on Apr. 16, 2014, now abandoned.

(51) Int. Cl.
*A61M 29/00* (2006.01)
*A61B 17/22* (2006.01)
(Continued)

(52) U.S. Cl.
CPC ........ *A61B 17/22* (2013.01); *A61B 17/22031* (2013.01); *A61F 2/013* (2013.01); *A61F 2/962* (2013.01); *A61F 2/966* (2013.01); *A61M 25/0021* (2013.01); *A61M 25/0074* (2013.01); *A61M 25/0082* (2013.01);
(Continued)

(58) Field of Classification Search
CPC .......... A61B 17/22; A61B 2017/22051; A61B 2017/22001; A61B 17/22031; A61B 2017/22047; A61F 2/966; A61F 2/962; A61F 2/013; A61M 2025/0004; A61M 2025/109; A61M 25/0082; A61M 25/0074; A61M 25/0021; A61M 25/104; A61M 2025/09125; A61M 2025/0042
See application file for complete search history.

(56) References Cited

U.S. PATENT DOCUMENTS 5,125,902 A  6/1992  Berry et al.
6,755,847 B2  6/2004  Eskuri et al.
(Continued)

FOREIGN PATENT DOCUMENTS

EP   2489335 A2   8/2012
WO   0121100 A1   3/2001
(Continued)

*Primary Examiner* — Amy R Weisberg
(74) *Attorney, Agent, or Firm* — Fortem IP LLP; Matthew Lincicum

(57) ABSTRACT

A system can comprise a catheter and a device having an elongate member and an expandable member. The expandable member can be coupled to the elongate member. The elongate member can extend through the catheter. The expandable member can be positioned with a proximal member end proximal to a distal catheter end, a distal member end positioned distal to the distal catheter end, and at least a portion of the expandable member between the distal catheter end and the distal member end in an expanded state in which a maximum transverse dimension of the expandable member is larger than a maximum transverse dimension of the distal member end. The catheter can be advanced in a patient's body with the expandable structure, in the expanded state, at the distal end of the catheter.

22 Claims, 3 Drawing Sheets

(51) Int. Cl.
*A61M 25/00* (2006.01)
*A61M 25/10* (2013.01)
*A61F 2/01* (2006.01)
*A61F 2/962* (2013.01)
*A61F 2/966* (2013.01)
*A61M 25/06* (2006.01)
*A61M 25/09* (2006.01)

(52) U.S. Cl.
CPC ...... *A61M 25/0662* (2013.01); *A61M 25/104* (2013.01); *A61B 2017/22001* (2013.01); *A61B 2017/22047* (2013.01); *A61B 2017/22051* (2013.01); *A61M 2025/0004* (2013.01); *A61M 2025/0042* (2013.01); *A61M 2025/0681* (2013.01); *A61M 2025/09125* (2013.01); *A61M 2025/09166* (2013.01); *A61M 2025/109* (2013.01)

(56) References Cited

U.S. PATENT DOCUMENTS

| | | |
|---|---|---|
| 7,052,500 B2 | 5/2006 | Bashiri et al. |
| 7,063,714 B2 | 6/2006 | Dorros et al. |
| 7,591,832 B2 | 9/2009 | Eversull et al. |
| 8,632,491 B2 | 1/2014 | Webler et al. |
| 2002/0077596 A1 | 6/2002 | McKenzie et al. |
| 2002/0161394 A1 | 10/2002 | Macoviak et al. |
| 2002/0173815 A1 | 11/2002 | Hogendijk et al. |
| 2005/0021075 A1 | 1/2005 | Bonnette et al. |
| 2005/0038421 A1 | 2/2005 | Joye et al. |
| 2005/0096692 A1 | 5/2005 | Linder et al. |
| 2005/0177187 A1 | 8/2005 | Gray et al. |
| 2005/0203569 A1 | 9/2005 | Kusleika et al. |
| 2005/0245866 A1 | 11/2005 | Azizi et al. |
| 2006/0155322 A1 | 7/2006 | Sater et al. |
| 2007/0005105 A1* | 1/2007 | Kusleika ............ A61B 17/221 606/200 |
| 2007/0006105 A1 | 1/2007 | Bartling et al. |
| 2007/0088384 A1 | 4/2007 | Vrba et al. |
| 2007/0156168 A1 | 7/2007 | Dunfee et al. |
| 2007/0179519 A1 | 8/2007 | Huisun et al. |
| 2009/0264859 A1* | 10/2009 | Mas ................... A61F 2/95 604/509 |
| 2009/0292297 A1 | 11/2009 | Ferrere et al. |
| 2010/0087908 A1 | 4/2010 | Hilaire et al. |
| 2011/0082493 A1 | 4/2011 | Samson et al. |
| 2011/0130657 A1 | 6/2011 | Chomas et al. |
| 2011/0202088 A1 | 8/2011 | Eckhouse et al. |
| 2011/0245841 A1 | 10/2011 | Shohat et al. |
| 2011/0319917 A1* | 12/2011 | Ferrera ............ A61B 17/12118 606/159 |
| 2012/0065660 A1 | 3/2012 | Ferrera et al. |
| 2012/0283760 A1 | 11/2012 | Sepetka et al. |
| 2013/0030460 A1 | 1/2013 | Marks et al. |
| 2013/0226223 A1* | 8/2013 | Spenser ................ A61F 2/013 606/200 |
| 2014/0207179 A1 | 7/2014 | Farhangnia et al. |
| 2014/0214003 A1 | 7/2014 | Yang et al. |
| 2014/0243881 A1 | 8/2014 | Lees et al. |
| 2014/0243882 A1 | 8/2014 | Ma et al. |
| 2014/0257362 A1 | 9/2014 | Eidenschink et al. |
| 2015/0150672 A1 | 6/2015 | Ma |
| 2015/0209557 A1* | 7/2015 | Tal ................. A61B 17/12109 600/435 |
| 2015/0257775 A1 | 9/2015 | Gilvarry et al. |
| 2015/0297250 A1 | 10/2015 | Farhat et al. |
| 2015/0327866 A1 | 11/2015 | Eckhouse et al. |
| 2016/0114138 A1 | 4/2016 | Jahrmarkt |

FOREIGN PATENT DOCUMENTS

| | | |
|---|---|---|
| WO | 0160442 A1 | 8/2001 |
| WO | 2006044632 A2 | 4/2006 |
| WO | 2013126299 A1 | 8/2013 |

\* cited by examiner

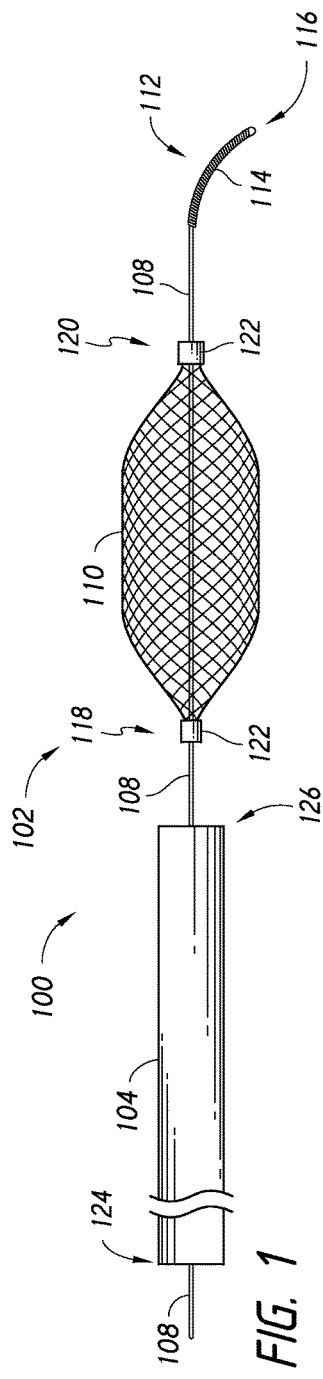
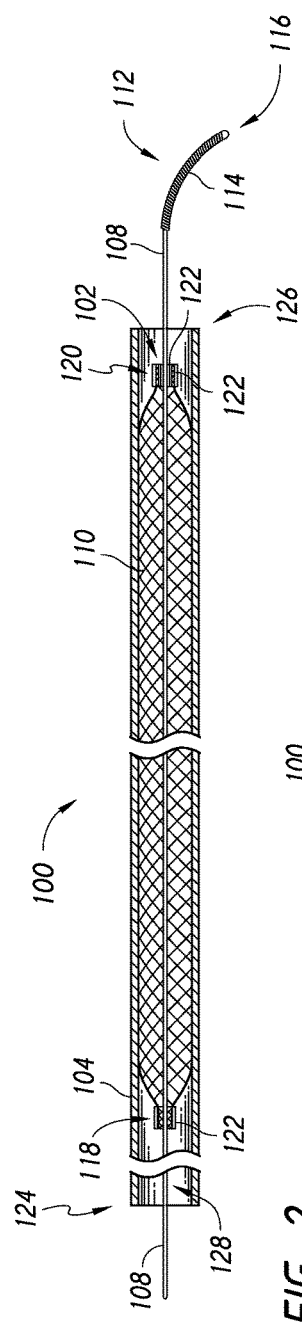
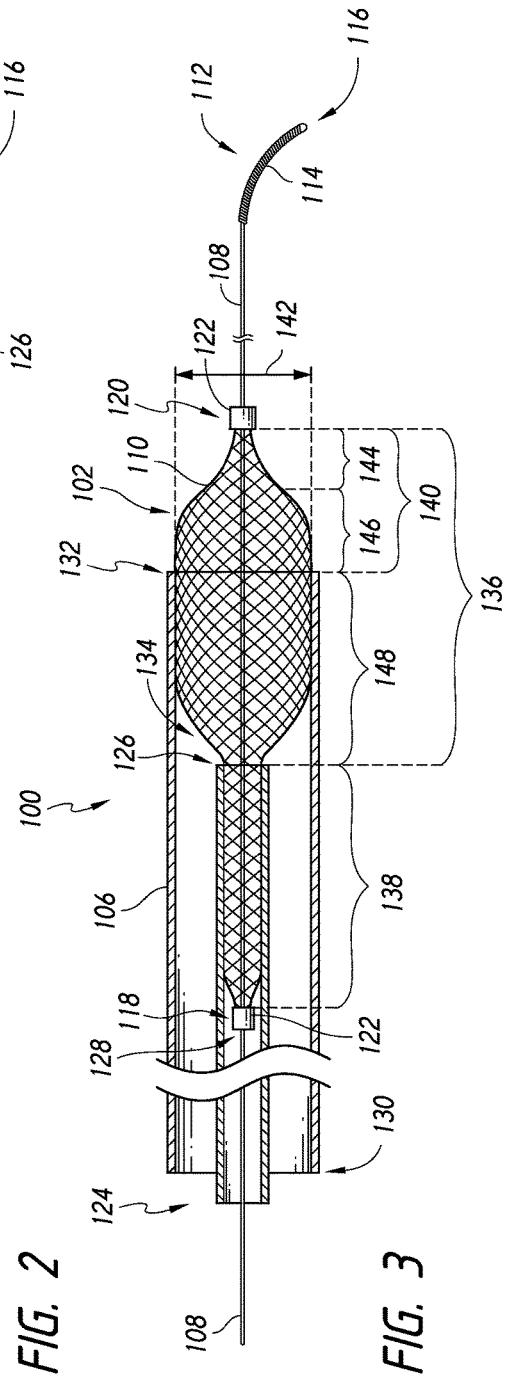
FIG. 1
FIG. 2
FIG. 3

SYSTEMS AND METHODS FOR CATHETER ADVANCEMENT

CROSS-REFERENCE TO RELATED APPLICATION

This application is a divisional of U.S. patent application Ser. No. 14/254,063, filed Apr. 16, 2014, the disclosure of which is incorporated hereon by reference in its entirety.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Various methods for delivering these intravascular stents are also known.

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion. Stent-like mechanical thrombectomy devices have been used to revascularize and/or remove occlusive thrombi.

Various intravascular therapies and other therapies can involve use of one or more catheters.

SUMMARY

Catheter advancement may be hindered, complicated, or both by the characteristics of the catheter used, e.g., a cross-sectional size of the catheter, and the characteristics of the anatomy through which the catheter is desired to be advanced, e.g., tortuosity and susceptibility to damage of the vessel.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1 or Clause 23. The other clauses can be presented in a similar manner.

1. A system comprising:
   a catheter comprising a distal catheter end and having a catheter lumen;
   a microcatheter comprising a distal microcatheter end and having a microcatheter lumen, the microcatheter being positioned at least partially within the catheter lumen with the distal microcatheter end positioned within the catheter lumen and proximal to the distal catheter end; and
   a device comprising:
      an elongate member extending within the microcatheter lumen; and
      an expandable member coupled to the elongate member and comprising a proximal member end and a distal member end, the proximal member end positioned proximal to the distal catheter end, the distal member end positioned distal to the distal catheter end, and at least a portion of the expandable member between the distal catheter end and the distal member end in an expanded state in which a maximum transverse dimension of the expandable member is larger than a maximum transverse dimension of the distal member end.

2. The system of Clause 1, wherein the portion of the expandable member is porous.

3. The system of Clause 1, wherein the portion of the expandable member comprises an outwardly concave section and an outwardly convex section, the outwardly convex section positioned between the outwardly concave section and the distal catheter end.

4. The system of Clause 1, wherein a longitudinal distance from the distal catheter end to the distal member end is greater than a maximum transverse dimension of the catheter lumen.

5. The system of Clause 1, wherein the maximum transverse dimension of the expandable member is approximately the same size as a characterizing transverse dimension of the catheter.

6. The system of Clause 5, wherein the maximum transverse dimension of the expandable member is at the location longitudinally aligned with the distal catheter.

7. The system of Clause 5, wherein the maximum transverse dimension of the expandable member is slightly smaller than a nominal inner diameter of the catheter to slightly larger than a nominal outer diameter of the catheter.

8. The system of Clause 1, wherein the maximum transverse dimension of the expandable member at the location longitudinally aligned with the distal catheter end is 95% of a maximum transverse dimension of the catheter lumen to 105% of a maximum transverse outer dimension of the catheter.

9. The system of Clause 1, wherein the expandable member comprises a braided plurality of strands.

10. The system of Clause 1, wherein a portion of the expandable member between the proximal member end and the distal catheter end is in an expanded state apposed to the inner catheter wall.

11. The system of Clause 1, wherein the proximal member end is positioned within the microcatheter lumen.

12. The system of Clause 1, wherein at least a portion of the expandable member is apposed against an inner wall of the microcatheter.

13. The system of Clause 1, wherein the expandable member is self-expanding.

14. The system of Clause 1, wherein the distal member end is slidably coupled to the elongate member.

15. The system of Clause 1, wherein the proximal member end is fixed to the elongate member.

16. The system of Clause 1, wherein the elongate member extends distally of the distal member end.

17. The system of Clause 16, wherein a segment of the elongate member distal to the distal member end has a curved shape in the absence of any externally applied force.

18. The system of Clause 16, wherein the elongate member extends through the expandable member.

19. The system of Clause 1, wherein a proximal end of the elongate member is positioned proximal to a proximal end of the microcatheter.

20. The system of Clause 1, wherein the elongate member has a total length greater than a total length of the microcatheter.

21. The system of Clause 1, wherein a proximal end of the microcatheter is positioned proximal to a proximal end of the catheter.

22. The system of Clause 1, wherein the microcatheter has a total length greater than a total length of the catheter.

23. A method for advancing a catheter, the method comprising:
(a) introducing a catheter into a vessel;
(b) positioning an expandable structure such that it extends distally from a distal end of the catheter;
(c) expanding at least a portion of the expandable structure distal to the distal end of the catheter to an expanded state;
(d), after (c), advancing the catheter while holding the expandable structure, in the expanded state, at the distal end of the catheter.

24. The method of Clause 23, wherein (b) further comprises advancing the expandable structure within the catheter.

25. The method of Clause 23, wherein, in (b), a portion of the expandable structure is positioned within the catheter while the expandable structure extends distally from the distal end of the catheter.

26. The method of Clause 25, further comprising expanding a portion of the expandable structure against an inner wall of the catheter.

27. The method of Clause 23, wherein the expandable member is configured for self-expansion, and (c) comprises allowing the portion of the expandable structure to expand.

28. The method of Clause 27, wherein (c) further comprises retracting a microcatheter from over the portion of the expandable structure such that the portion self-expands.

29. The method of Clause 23, further comprising injecting a fluid through the expandable structure while holding the expandable structure, in the expanded state, at the distal end of the catheter.

30. The method of Clause 29, wherein the fluid is an intravascular contrast agent.

31. The method of Clause 23, wherein (d) comprises advancing the catheter from the vessel into a branch vessel while holding the expandable structure, in the expanded state, at the distal end of the catheter.

32. The method of Clause 23, wherein (d) comprises advancing the catheter from an aortic arch into a brachiocephalic branch while holding the expandable structure, in the expanded state, at the distal end of the catheter.

33. The method of Clause 23, wherein (d) comprises advancing the catheter through a type III aortic arch while holding the expandable structure, in the expanded state, at the distal end of the catheter.

34. The method of Clause 23, wherein (d) comprises advancing the catheter through a stricture in the vessel while holding the expandable structure, in the expanded state, at the distal end of the catheter.

35. The method of Clause 23, wherein (d) comprises advancing the catheter through a bend in the vessel while holding the expandable structure, in the expanded state, at the distal end of the catheter.

36. The method of Clause 23, wherein the expandable structure is coupled to an elongate member, the method further comprising manipulating the elongate member to guide the catheter.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1 illustrates a microcatheter and an expandable member entirely positioned distal to a distal end of the microcatheter, according to an embodiment.

FIG. 2 illustrates the microcatheter and the expandable member of FIG. 1, with the expandable member entirely positioned within a lumen of the microcatheter, according to an embodiment.

FIG. 3 illustrates a system comprising a catheter, a microcatheter, and an expandable member, according to an embodiment.

DETAILED DESCRIPTION

Figure 6:
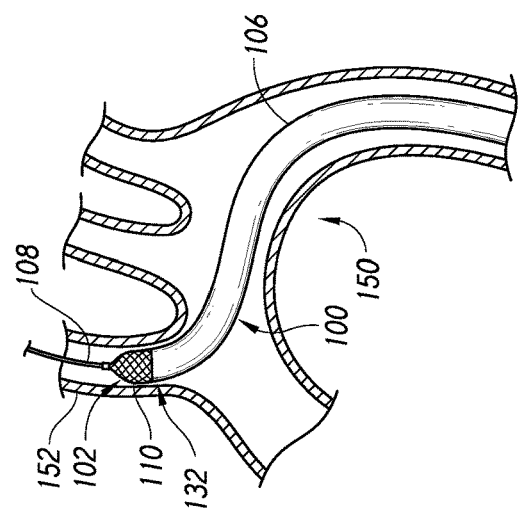
FIG. 6 illustrates the catheter and the expandable member of FIGS. 4 and 5 with the distal end of the catheter positioned in the brachiocephalic branch, according to an embodiment.

The detailed description set forth below is intended as a description of various configurations of the subject technology and is not intended to represent the only configurations in which the subject technology may be practiced. The detailed description includes specific details for the purpose of providing a thorough understanding of the subject technology. However, the subject technology may be practiced without these specific details. In some instances, well-known structures and components are not shown, or are shown schematically or in block diagram form, to avoid obscuring the concepts of the subject technology.

Various embodiments of systems and methods for advancing catheters are disclosed. Some of the embodiments have particular advantage in advancing catheters through tortuous vessels, past fragile tissue, or both. Various other features and advantages of embodiments are discussed in shown herein.

In some embodiments, a system is provided that can comprise an expandable device and one or more catheters, of which some or all may be microcatheters. FIGS. 1 and 2 illustrate an exemplifying embodiment of a system 100 comprising an expandable device 102 and a microcatheter 104. FIG. 3 illustrates an exemplifying embodiment of a system 100 comprising an expandable device 102, a microcatheter 104, and a catheter 106.

In some embodiments, an expandable device 102 can comprise an elongate manipulation member 108 and an expandable member 110. The elongate manipulation member 108 can be movable within the catheter and/or microcatheter to position the expandable member 110 at a desired location. The elongate manipulation member can be sufficiently flexible to allow manipulation, e.g., advancement and/or retraction, of the expandable device 102 through tortuous passages. Tortuous passages can include, for example, catheter lumens, microcatheter lumens, blood vessels, urinary tracts, biliary tracts, and airways. The elongate manipulation member can be formed of any material and in any dimensions suitable for the task(s) for which the system is to be employed. In some embodiments, the elongate manipulation member can comprise a metal wire. In some embodiments, the elongate manipulation member can comprise stainless steel, nitinol, or other metal or alloy. In some embodiments, the elongate member can be surrounded over some or all of its length by a coating, such as, for example, polytetrafluoroethylene.

In some embodiments, the elongate manipulation member 108 can comprise a distal section 112 surrounded by a flexible helically wound coil 114. The helically wound coil can comprise radiopaque material to facilitate visualization via radiographic imaging. The distal section can extend proximally from a distal end 116 of the elongate manipulation member in some embodiments. Additionally or alternatively to the inclusion of flexible helically wound coil, the distal section can have a curved shape, for example as illustrated in FIGS. 1-3, such that the distal section of the elongate manipulation member can be used to guide advancement of the distal end of the elongate manipulation member.

In some embodiments, the expandable member 110 can be made of two or more filaments. In some embodiments, the expandable member can be braided, woven, or cut from a sheet or tube. The filaments can be formed of known flexible materials including shape memory materials (e.g., nitinol), cobalt chromium, platinum, stainless steel, other metals, other metal alloys, or a combination thereof. In some embodiments, the filaments can be wire having a round, ovoid, square, rectangular, or other shape in cross-section. Further, the filaments can be configured such that the expandable member 110 is self-expanding. In some embodiments, at least a portion of the expandable member will tend to resiliently assume an expanded configuration in the absence of countervailing force. In some embodiments, the expandable member can be fabricated from a first group of filaments formed from platinum or platinum alloy (e.g., platinum/8% tungsten) braided with a second group of filaments formed from cobalt-nickel or cobalt-chromium alloy (e.g., 35N LT™ available from Fort Wayne Metals of Fort Wayne, Ind., USA). In other embodiments, one or more of the filaments can be formed of a biocompatible metal material or a biocompatible polymer.

The wire filaments can be braided into a resulting lattice-like structure having tubular configuration with both ends open before attachment to the elongate manipulation member 108. In at least one embodiment, during braiding or winding of the expandable member, the filaments can be braided using a 1-over-2-under-2 pattern. In other embodiments, however, other methods of braiding can be followed, without departing from the scope of the disclosure. Such other braiding methods can include a 1-over-1-under-1 pattern and 2-over-2-under-2 pattern. In some embodiments, the expandable member can be heat set to a desired shape, such as, for example, by placing the expandable member in contact with a molding surface of a molding element which defines a desired shape of all or a portion of the expandable member.

The expandable member 110 can comprise pores. In some embodiments, the pores can have a size sufficient to allow fluid pass therethrough. For example, the pores can permit intravascular contrast agents to be introduced into a patient's body through the pores when the expandable member 110 is an expanded state. In some embodiments, the expandable member can exhibit a porosity configured to reduce haemodynamic flow through the expandable member to a desired extent. For example, if the expandable member is formed of a braid, the sizes of the pores can be controlled by adjusting the numbers of wires in the braid and the pick and pitch of the braid. As will be appreciated, the porosity of the expandable member can be adjusted by "packing" the expandable member during deployment, as known in the art. In some embodiments, the expandable member can substantially obstruct flow or can be substantially flow transparent.

In some embodiments, the expandable member 110, whether or not it comprises a plurality of filaments, can be coated with one or more compounds, such as, for example, antithrombotic agents.

Information regarding additional embodiments, features, and other details of expandable members, methods of use, and other components that can optionally be used or implemented in embodiments of the devices and systems described herein, can be found in U.S. Patent Application Publication No. 2009/0287288, published on Nov. 19, 2009; and U.S. Pat. No. 7,300,458, entitled Medical Implant Having a Curable Matrix Structure, issued Nov. 27, 2007; the entireties of each of which are incorporated herein by reference.

Figures 7, 8:
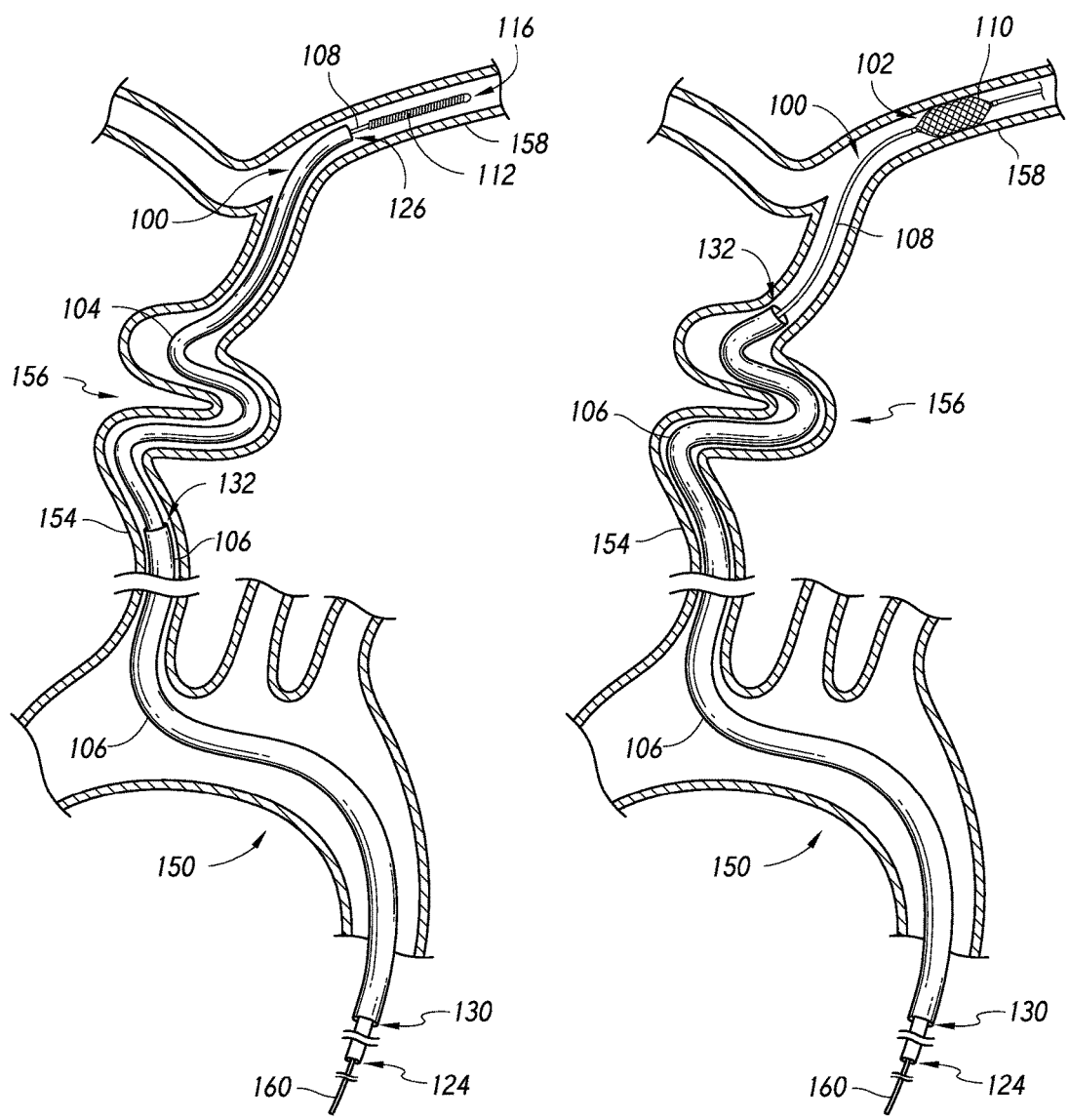
FIG. 7 illustrates a distal end of a catheter positioned in a common carotid artery proximal to a carotid siphon with a distal end of a microcatheter and a distal end of an expandable device both positioned distal to the carotid siphon in a middle cerebral artery, according to an embodiment.
FIG. 8 illustrates the microcatheter of FIG. 7 retracted to expose an expandable member of the expandable device, the expandable member expanded within the middle cerebral artery, and the distal end of the catheter being advanced through the carotid siphon, according to an embodiment.

As illustrated for example in FIG. 1, a proximal end 118 and a distal end 120 of the expandable member 110 can be coupled to the elongate manipulation member 108. The proximal end 118 of the expandable member can be fixedly attached to the elongate manipulation member, e.g., such that the proximal end does not move substantially relative to the elongate member during its intended use. The distal end 120 of the expandable member can be slidably attached to the elongate manipulation member, e.g., such that the distal end is permitted to translate along at least a portion of the elongate member during its intended use. The proximal and 118, the distal end 120, or both can be coupled to the elongate manipulation member 108 by one or more bands 122. The bands 122 can comprise radiopaque material, e.g., gold, platinum, etc., to aid visualization via radiographic imaging. In some embodiments, one or both of the bands 122 can comprise a tube with an inside diameter larger than the outside diameter of the elongate manipulation member 108, so that the band(s) are slidable over the member 108. The expandable member 110 can be constructed as a braided tube, as discussed herein, and each end of the braided tube can be attached (by welding, crimping, adhesives or otherwise) to one of the bands 122. Thus is created an expandable member 110 with inward-tapering proximal and distal ends as seen in FIGS. 1, 3 and 8. The expandable member 110 can then be attached to the elongate member 108 by sliding the bands 122 over the member 108, and fixing one or both of the bands 122 to the member 108, by welding, crimping, adhesives, etc. In various embodiments, only one of the bands 122 is fixed to the elongate member 108 so that the unfixed band is slidable over the member 108 as described herein. For example, the proximal band can be fixed and the distal band can be unfixed and slidable, or vice versa Sections of the expandable member 110 at or near the proximal end 118 and/or the distal end 120 can be shaped to provide an atraumatic transition from the end to a periphery of the expandable member when the expandable member is an expanded condition, for example as discussed below.

Each of the microcatheter 104 and the catheter 106, in embodiments in which they are employed respectively, can be configured to be introduced and advanced through one or more vessels of a patent, such as, for example, blood vessels, urinary tracts, biliary tracts, and airways. Each of the microcatheter 104 and the catheter 106, in embodiments in which they are employed respectively, can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other plastic coating. Additionally, either surface can be coated with various combinations of different materials, depending upon the desired results.

As illustrated for example in FIGS. 1-3, the microcatheter 104 can comprise a proximal end 124, distal end 126, and a lumen 128 extending between the proximal end 124 and the distal end 126. A length of the microcatheter between the proximal end 124 and the distal end 126 can be sufficient to extend from a location outside of a patient to a target site within the patient. In some embodiments, the microcatheter can have a nominal inner diameter equal to or less than 0.045 in., 0.040 in., 0.035 in, 0.030 in., 0.027 in., 0.021 in., or 0.017 in. In some embodiments, the nominal inner diameter of the microcatheter can be 0.010 in. to 0.040 in. In some embodiments, the nominal inner diameter of the microcatheter can be 0.015 in. to 0.035 in. In some embodiments, the nominal inner diameter of the microcatheter can be 0.017 in., 0.021 in., 0.027 in., or 0.032 in. In some embodiments, the nominal inner diameter of the microcatheter can correspond to a nominal inner diameter of the microcatheter at the distal end 126. In some embodiments, the microcatheter can have a nominal outer diameter equal to or less than 3.5 French (Fr), 3.2 Fr, 3.0 Fr, 2.5 Fr, 2.0 Fr, or 1.7 Fr. In some embodiments, the nominal outer diameter of the microcatheter can be 1.5 Fr to 3.5 Fr. In some embodiments, the nominal outer diameter of the microcatheter can be 1.7 Fr to 3.2 Fr. In some embodiments, the nominal outer diameter of the microcatheter can be 1.7 Fr or 3.2 Fr. In some embodiments, the nominal outer diameter of the microcatheter can correspond to a nominal outer diameter of the microcatheter at the distal end 126.

As illustrated for example in FIG. 3, the catheter 106 can comprise a proximal end 130, distal end 132, and a lumen 134 extending between the proximal end 130 and the distal end 132. A length of the catheter between the proximal end 130 and the distal end 132 can be sufficient to extend from a location outside of a patient to a target site within the patient. In some embodiments, the catheter can have a nominal inner diameter equal to or greater than 0.080 in., 0.072 in., 0.070 in, 0.060 in., 0.050 in., 0.058 in., or 0.050 in. In some embodiments, the nominal inner diameter of the catheter can be 0.050 in. to 0.090 in. In some embodiments, the nominal inner diameter of the catheter can be 0.058 in. to 0.072 in. In some embodiments, the nominal inner diameter of the catheter can be 0.058 in. or 0.072 in. In some embodiments, the nominal inner diameter of the catheter can correspond to a nominal inner diameter of the catheter at the distal end 132. In some embodiments, the catheter can have a nominal outer diameter equal to or greater than 0.060 in., 0.070 in., 0.084 in., or 0.090 in. In some embodiments, the nominal outer diameter of the catheter can be 0.060 in. to 0.100 in. In some embodiments, the nominal outer diameter of the catheter can be 0.070 in. to 0.840 in. In some embodiments, the nominal outer diameter of the catheter can be 0.070 in. or 0.840 in. In some embodiments, the nominal outer diameter of the catheter can correspond to a nominal outer diameter of the catheter at the distal end 132. In some embodiments, the catheter 106 can comprise an inflatable balloon at or near the distal end 132.

Although exemplifying dimensions have been provided for the microcatheter 104 and the catheter 106, these dimensions are provided solely as examples. The microcatheter and the catheter can be sized such that the microcatheter can be delivered through the catheter to a location in a patient's body. Also, although the microcatheter 104 and the catheter 106 are illustrated as having constant or substantially constant cross-sectional dimensions, either or both of the microcatheter 104 and the catheter 106 can have cross-sectional dimensions that increase between the distal end and the proximal end, being larger at or near the proximal end than at or near the distal end.

The elongate manipulation member 108, the microcatheter 104, and the catheter 106 can be moved relative to each other to expand or contract the expandable member 110. As illustrated for example in FIGS. 1 and 2, the elongate manipulation member and the microcatheter can be operated to expand and contract the expandable member. The expandable member 110 can be collapsed and positioned within the lumen 128 of the microcatheter 104 by proximally retracting the elongate manipulation member while holding the microcatheter 104 substantially stationary, distally advancing the microcatheter while holding the elongate manipulation member stationary, or proximally retracting the elongate manipulation member while distally advancing the microcatheter. Conversely, the expandable member 110 can be expanded by distally advancing the elongate manipulation member while holding the microcatheter 104 substantially stationary, proximally retracting the microcatheter while holding the elongate manipulation member stationary, or distally advancing the elongate manipulation member while proximally retracting the microcatheter.

Figure 4:
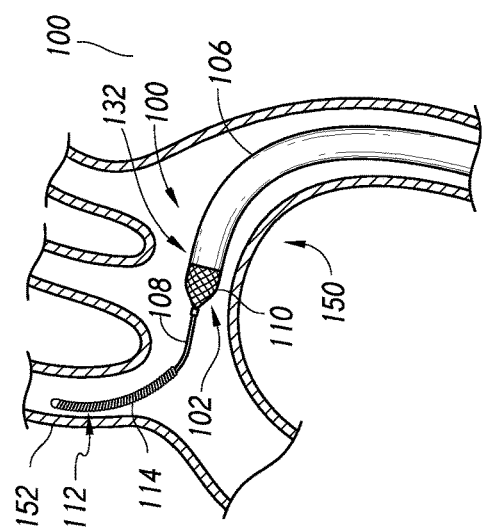
FIG. 4 illustrates a distal end of a catheter positioned in an aortic arch with at least a portion of an expandable member positioned distally adjacent to the distal end of the catheter, according to an embodiment.

In some embodiments, the expandable device 102 can reduce a risk of damaging tissue adjacent to the catheter during advancement of the catheter, can facilitate catheter advancement, or both. For example, FIG. 4 illustrates the distal end 132 of the catheter positioned in an aortic arch 150 with at least a portion of the expandable member 110 extending distally from the distal end of the catheter and in an expanded state, according to an embodiment. In some embodiments, the expandable member 110 is positioned extending distally from the distal end of the catheter in an expanded state after the distal end 132 of the catheter is positioned in the aortic arch. In some embodiments, the expandable member 110 is positioned extending distally from the distal end of the catheter in an expanded state before the distal end 132 of the catheter is advanced into the aortic arch. The expandable device 102 can be advanced in the catheter 106, the microcatheter 104, or both before, after, or while the distal end 132 of the catheter is positioned within the aortic arch 150. If present, the microcatheter 104 can be advanced in the catheter 106 before, after, or while the distal end 132 of the catheter is positioned within the aortic arch 150, and may be advanced in the catheter 106 together with the expandable device 102, or before or after advancement of the expandable device 102 in the catheter 106. In some embodiments, the distal end 126 of the microcatheter 104 is moved distally of the distal end 132 of the catheter 106 in advance of movement of the expandable member 110 distal to the distal end 132 of the catheter, or moved with the expandable member 110 to a location distal to the distal end 132 of the catheter 106. The microcatheter 104 and the expandable device can be manipulated to expand the expandable member 110 by proximal movement of the microcatheter, distal advancement of the expandable device, or both.

The expandable device 102 and the catheter 106 can be configured and positioned, for example, as shown in FIG. 3. FIG. 3 illustrates the elongate manipulation member 108 extending within the lumen 128 of the microcatheter 104, the proximal end 118 of the expandable member 110 positioned proximal to the distal end 132 of the catheter 106, and the distal end 120 of the expandable member positioned distal to the distal end 132 of the catheter. A segment 136 of the expandable member 110 is shown in an expanded state compared to a segment 138 of the expandable member collapsed within the lumen 128 of the microcatheter. A portion 140 of the expandable member between the distal catheter end and the distal member end tapers between (a) a location of apposition between the expandable member and the catheter and (b) the distal end 120 of the expandable member. In some embodiments, the portion 140 can facilitate atraumatic advancement of the distal end 132 of the catheter. In some embodiments, the portion 140 can have a maximum transverse dimension 142 larger than a maximum transverse dimension of the distal end 120 of the expandable member. In some embodiments, the maximum transverse dimension 142 can be at a location longitudinally aligned with the distal end 132 of the catheter, for example, as illustrated in FIG. 3.

In some embodiments, a length of the portion 140, i.e., a distance from the distal end 132 of the catheter 106 to the distal end 120 of the expandable member 110, is greater than a maximum transverse dimension of the catheter lumen. The maximum transverse dimension of the catheter lumen can be a nominal dimension, such as, for example, a nominal diameter. In some embodiments, a ratio of the length of the portion 140 to the maximum transverse dimension of the catheter lumen can be, for example, 0.5 or greater, 0.75 or greater, 1 or greater, 1.5 or greater, 2 or greater, or 3 or greater.

In some embodiments, the maximum transverse dimension 142 of the portion 140 can be approximately the same size as a characterizing transverse dimension of the catheter. In some embodiments, the maximum transverse dimension 142 is slightly smaller than a nominal inner diameter of the catheter to slightly larger than a nominal outer diameter of the catheter. For example, the maximum transverse dimension 142 can be larger than a nominal inner diameter of the catheter where the maximum transverse dimension 142 occurs distal to the distal end 132 of the catheter. In some embodiments, the maximum transverse dimension 142 is 95% of a maximum transverse dimension of the catheter lumen to 105% of a maximum transverse outer dimension of the catheter.

The portion 140 of the expandable member 110 can comprise an outwardly concave section 144 and an outwardly convex section 146. The outwardly convex section can be 146 positioned between the outwardly concave section 144 and the distal end 132 of the catheter 106. In some embodiments, such a shape can further facilitate atraumatic advancement of the distal end 132 of the catheter.

A portion 148 of the expandable member 110 can be positioned outside of the microcatheter 104 and within the catheter 106. The portion 148 can be apposed against an inner wall of the lumen 134 of the catheter. The portion 148 can inhibit movement of the expandable member 110 relative to the catheter 106 during advancement of the expandable member and the catheter together within a patient's body. In various embodiments, a segment 138 of the expandable member may or may not be retained within the microcatheter 104. In some embodiments, the expandable member 110 can be positioned relative to the distal end 132 of the catheter 106 as disclosed herein with the microcatheter 104 omitted.

In some embodiments, when the expandable member 110 is positioned across the distal end 132 of the catheter 106, a substance can be infused through the lumen 134 of the catheter and the pores of the expandable member into a vessel of a patient's body. The substance can comprise, for example, an intravascular contrast agent to aid visualization using imaging.

The catheter 106 and the expandable device 102 can be advanced from the aortic arch 150 with at least a portion of the expandable member 110 extending distally from the distal end 132 of the catheter. In some embodiments, wherein the distal section 112 of the elongate manipulation member 108 is shaped to be used to guide, the distal section 112 can be used to guide the distal end 132 through the vasculature. For example, the distal section 112 of the elongate manipulation member can be rotated to direct the system into the brachiocephalic branch 152 from the aortic arch 150.

Figure 5:
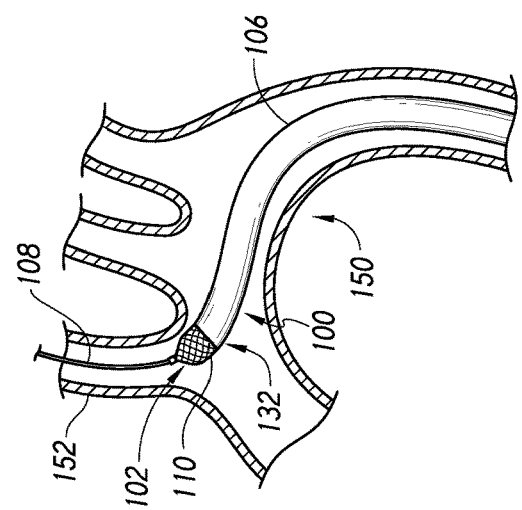
FIG. 5 illustrates the catheter and the expandable member of FIG. 4 entering the brachiocephalic branch from the aortic arch, according to an embodiment.

FIG. 5 illustrates the catheter 106 and the expandable device 102 entering the brachiocephalic branch 152 from the aortic arch 150, according to an embodiment. In some embodiments, the expandable device 102 and the catheter 106 can be held stationary or substantially stationary relative to each other. For example, relative movement of the proximal end of the elongate manipulation member 108 and the proximal end of the catheter 106 can be inhibited or prevented while advancing the catheter 106 and the expandable device 102 together. As they enter the brachiocephalic branch, the portion 140 of the expandable member 110, which extends distally from the distal end 132 of the catheter, provides an atraumatic transition from the elongate manipulation member 108 to the distal end 132 of the catheter. The portion 140 may facilitate advancement of the distal end 132, inhibit or prevent the distal end 132 from damaging the tissue along the path of advancement of the distal end 132 (as may happen, for example, if the rim of the distal end 132 strikes the upper wall of the arch 150, or any of the ostia of the branch vessels extending from the arch 150), or both as the distal end 132 is urged distally toward the brachiocephalic branch 152. FIG. 6 illustrates the distal end 132 of the catheter 106 and the portion 140 of the expandable member 110 positioned in the brachiocephalic branch 152.

Although use of the expandable device 102 to reduce a risk of damaging tissue adjacent to the catheter during advancement of the catheter, to facilitate catheter advancement, or both, has been shown and described with reference to advancement of a catheter from an aortic arch to brachiocephalic branch, such disclosure is provided only by way of example. The expandable device 102 can be operated in the same or similar manner to provide some or all of these benefits in other locations within the body. For example, the expandable device 102 and the catheter 106 can be used to move the catheter in a type III aortic arch.

In some embodiments, the expandable device 102 can be used to facilitate or permit advancement of a catheter in tortuous vessels and/or in smaller vessels than would otherwise be possible, practical, safe, or a combination thereof without use of additional instruments. In some instances, it may be desirable to advance a catheter as close as possible to a treatment location. For example, when treating a patient suffering a thromboembolic stroke, it may be desirable to place a distal end of a catheter as close as possible to the site of the thrombus. However, it may be difficult, impractical, unsafe, and/or impossible to advance the distal end of the catheter close to or into small vessels (e.g., the middle cerebral artery and anterior cerebral artery) and/or through tortuous passages (e.g., the carotid siphon).

FIG. 7 illustrates the distal end 132 of the catheter 106 positioned in a common carotid artery 154 proximal to a carotid siphon 156. In some embodiments, the catheter 106 is advanced from the aortic arch 150 into the brachiocephalic branch 152, and into the common carotid artery 154 using the techniques disclosed herein with the expandable member 110 expanded and extending distally from the distal end 132 of the catheter. FIG. 7 shows the distal end 126 of the microcatheter 104 having been advanced through the carotid siphon 156 into the middle cerebral artery 158. The expandable device 102 is also shown with the distal end 116 of the elongate manipulation member 108 positioned in the middle cerebral artery. In some embodiments, the expandable device 102 and the microcatheter 104 together can be advanced distally of the distal end 132 of the catheter 106, e.g., through the carotid siphon and into the middle cerebral artery. In some embodiments, wherein the distal section 112 of the elongate manipulation member 108 is shaped to be used to guide, the distal section 112 can be used to guide the expandable device 102 and the microcatheter 104 through the vasculature. For example, the distal section 112 of the elongate manipulation member can be rotated to direct the expandable device 102 and the microcatheter 104 through the bends of the carotid siphon 156 and into a desired branch vessel, e.g., the middle cerebral artery or anterior cerebral artery.

The expandable member 110 can be expanded at a location distal to the distal end 132 of the catheter 106. For example, the expandable member 110 is positioned distal to the carotid siphon 156 in some embodiments. In some embodiments, the expandable member 110 is expanded within the middle cerebral artery 158, as illustrated, for example, in FIG. 8. The expandable device 102 and the microcatheter 104 can be manipulated to expand the expandable member 110 by proximal movement of the microcatheter, distal advancement of the expandable device, or both.

Advantageously, in embodiments wherein the expandable member 110 comprises pores, the expandable member 110 can permit fluid, e.g., blood, to flow through the expandable member while it is expanded against a vessel wall.

While the expandable member 110 is expanded against the vessel wall, the expandable member can inhibit proximal movement of the expandable device 102. The catheter 106 can be advanced distally while proximally pulling a section 160 of the elongate manipulation member 108 proximal to the distal end 132 of the catheter 106, e.g, outside of the patient's body. The elongate manipulation member 108 is placed in tension between the section 160 and the expandable member 110. While proximally pulling the section 160 and with the expandable member 110 expanded against the vessel wall, the catheter 106 can be advanced distally. For example, FIG. 8 illustrates the expandable member 110 expanded within the middle cerebral artery 158 and the catheter 106 being advanced over the elongate manipulation member 108 through the carotid siphon 156, thereby using the elongate manipulation member 108 as a guide.

In some embodiments, for example as illustrated in FIG. 8, the microcatheter 104 can be retracted proximally of the distal end 132 of the catheter prior to advancement of the catheter 106 to allow the distal end 132 of the catheter to engage directly and to follow along the elongate manipulation member 108. In some embodiments, the microcatheter 104 can be held stationary or substantially stationary (e.g., held at its proximal end) with the distal end 126 of the microcatheter 104 positioned distal to the distal end 132 of the catheter 106 while the catheter is advanced distally.

Although use of the expandable device 102 to facilitate or permit advancement of a catheter in tortuous vessels and/or into smaller vessels than would otherwise be possible, practical, safe, or a combination thereof without use of additional instruments has been shown and described with reference to advancement of a catheter from a common carotid artery through a carotid siphon, such disclosure is provided only by way of example. The expandable device 102 can be operated in the same or similar manner to provide some or all of these benefits in other locations within the body.

The apparatuses and methods discussed herein are not limited to use within any particular vessels, but may include any number of different types of vessels. For example, in some aspects, the vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyro cervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

The apparatuses and methods discussed herein are not limited to use within the vascular system but may include any number of further treatment applications. Other treatment sites may include areas or regions of the body such as organ bodies.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method for advancing a catheter, the method comprising:
    (a) introducing a catheter into a vessel and positioning a microcatheter within a lumen of the catheter;
    (b) positioning an expandable structure such that a first portion of the expandable structure is positioned within the catheter while a second portion of the expandable structure extends distally from a distal end of the catheter;
    (c) after (b), expanding at least the second portion of the expandable structure distal to the distal end of the catheter to an expanded state;
    (d), after (c), advancing both the catheter and the expandable structure while holding the expandable structure, in the expanded state, at the distal end of the catheter,
    (e) distally advancing the microcatheter relative to the expandable structure, or proximally retracting the expandable structure relative to the microcatheter, to collapse the expandable structure within the microcatheter; and
    (f) after (e), proximally retracting both the expandable structure and the microcatheter relative to the catheter.

2. The method of claim 1, wherein the expandable member is configured for self-expansion, and (c) comprises allowing the portion of the expandable structure to expand.

3. The method of claim 1, further comprising injecting a fluid through the expandable structure while holding the expandable structure, in the expanded state, at the distal end of the catheter.

4. The method of claim 3, wherein the fluid is an intravascular contrast agent.

5. The method of claim 1, wherein (d) comprises advancing the catheter from the vessel into a branch vessel while holding the expandable structure, in the expanded state, at the distal end of the catheter.

6. The method of claim 1, wherein (d) comprises advancing the catheter from an aortic arch into a brachiocephalic branch while holding the expandable structure, in the expanded state, at the distal end of the catheter.

7. The method of claim 1, wherein, after (c), a portion of the expandable structure extends proximally of the distal end of the catheter.

8. The method of claim 1, wherein, after (c), a maximum transverse dimension of the expandable structure is larger than a maximum transverse dimension of a distal end of the expandable structure.

9. The method of claim 1, wherein, after (c), a maximum transverse dimension of the expandable structure is approximately the same size as a characterizing transverse dimension of the catheter.

10. The method of claim 1, wherein, in (b), a proximal end of the expandable structure is coupled to an elongate member via a proximal band comprising a tube.

11. The method of claim 1, wherein, in (b), a distal end of the expandable structure is coupled to an elongate member via a proximal band comprising a tube.

12. The method of claim 1, wherein (c) further comprises retracting the microcatheter from over the first and second portions of the expandable structure such that the first and second portions self-expand.

13. A method for advancing a catheter, the method comprising:
(a) introducing a catheter into a vessel and positioning a microcatheter within a lumen of the catheter;
(b) positioning an expandable structure such that it extends distally from a distal end of the catheter;
(c) expanding at least a portion of the expandable structure distal to the distal end of the catheter to an expanded state;
(d) after (c), advancing the catheter and the expandable structure together from the vessel into a branch vessel while holding the expandable structure, in the expanded state, at the distal end of the catheter;
(e) distally advancing the microcatheter relative to the expandable structure, or proximally retracting the expandable structure relative to the microcatheter, to collapse the expandable structure within the microcatheter, and
(f) after (e), proximally retracting both the expandable structure and the microcatheter relative to the catheter.

14. The method of claim 13, wherein, in (b), a portion of the expandable structure is positioned within the catheter while the expandable structure extends distally from the distal end of the catheter.

15. The method of claim 13, wherein the expandable member is configured for self-expansion, and (c) comprises allowing the portion of the expandable structure to expand.

16. The method of claim 13, further comprising injecting a fluid through the expandable structure while holding the expandable structure, in the expanded state, at the distal end of the catheter.

17. The method of claim 13, wherein the fluid is an intravascular contrast agent.

18. The method of claim 13, wherein (d) comprises advancing the catheter from an aortic arch into a brachiocephalic branch while holding the expandable structure, in the expanded state, at the distal end of the catheter.

19. The method of claim 13, wherein, after (c), a portion of the expandable structure extends proximally of the distal end of the catheter.

20. The method of claim 13, wherein, after (c), a maximum transverse dimension of the expandable structure is larger than a maximum transverse dimension of a distal end of the expandable structure.

21. The method of claim 13, wherein, after (c), a maximum transverse dimension of the expandable structure is approximately the same size as a characterizing transverse dimension of the catheter.

22. The method of claim 13, wherein (c) further comprises retracting the microcatheter from over the first portion of the expandable structure such that the portion self-expands.

* * * * *